(12) United States Patent
Fukushima

(10) Patent No.: US 10,912,444 B2
(45) Date of Patent: Feb. 9, 2021

(54) IMAGE PROCESSING APPARATUS, IMAGE PROCESSING METHOD, AND ENDOSCOPE

(71) Applicant: OLYMPUS CORPORATION, Tokyo (JP)

(72) Inventor: Ikutoshi Fukushima, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 72 days.

(21) Appl. No.: 16/108,634

(22) Filed: Aug. 22, 2018

(65) Prior Publication Data

US 2018/0353053 A1 Dec. 13, 2018

Related U.S. Application Data

(63) Continuation of application No. PCT/JP2016/055303, filed on Feb. 23, 2016.

(51) Int. Cl.
*A61B 1/00* (2006.01)
*G06T 7/62* (2017.01)
(Continued)

(52) U.S. Cl.
CPC ........ *A61B 1/00009* (2013.01); *A61B 1/0005* (2013.01); *A61B 1/00096* (2013.01);
(Continued)

(58) Field of Classification Search
CPC . A61B 1/00009; A61B 5/066; A61B 1/00179; A61B 1/00193; A61B 1/0005;
(Continued)

(56) References Cited

U.S. PATENT DOCUMENTS

2009/0309961 A1* 12/2009 Miyashita ............ G06K 9/6251
348/65
2010/0061597 A1* 3/2010 Kanda .................... A61B 1/041
382/107

(Continued)

FOREIGN PATENT DOCUMENTS

JP H03080824 A 4/1991
JP H05340721 A 12/1993

(Continued)

OTHER PUBLICATIONS

International Search Report dated May 24, 2016 issued in PCT/JP2016/055303.

*Primary Examiner* — Yon J Couso
(74) *Attorney, Agent, or Firm* — Scully, Scott, Murphy & Presser, P.C.

(57) ABSTRACT

In order to acquire height information regarding a subject disposed on the internal surface of an elongated tubular member, an image processing apparatus according to the present disclosure, includes a processor the processor including hardware and configured to perform the steps of receiving a first image and a second image acquired from a subject using an optical system having a field of view in a direction of at least about 90° to a central axis of the optical system, the first image acquired at a first position, the second image acquired at a second position, the second position different from the first position along the central axis; and calculating a distance between the subject and the central axis of the optical system, based on a distance between the first position and the second position, and based on the corresponding points in the third image and in the fourth image.

9 Claims, 14 Drawing Sheets

(51) Int. Cl.
     *G02B 23/24*   (2006.01)
     *G02B 5/00*    (2006.01)
     *A61B 5/06*    (2006.01)
     *A61B 1/05*    (2006.01)
(52) U.S. Cl.
     CPC ...... *A61B 1/00163* (2013.01); *A61B 1/00179* (2013.01); *A61B 1/00193* (2013.01); *A61B 1/05* (2013.01); *A61B 5/066* (2013.01); *G02B 5/001* (2013.01); *G02B 23/2415* (2013.01); *G02B 23/2423* (2013.01); *G02B 23/2484* (2013.01); *G06T 7/62* (2017.01); *A61B 1/00112* (2013.01); *A61B 2576/00* (2013.01); *G02B 23/2407* (2013.01); *G06T 2207/10068* (2013.01)
(58) Field of Classification Search
     CPC ... A61B 1/05; A61B 1/00163; A61B 1/00096; A61B 2576/00; A61B 1/00112; G02B 23/2415; G02B 23/2484; G02B 5/001; G02B 23/2423; G02B 23/2407; G06T 7/62; G06T 2207/10068
     See application file for complete search history.

(56)         References Cited

U.S. PATENT DOCUMENTS

| | | | |
|---|---|---|---|
| 2011/0237884 A1* | 9/2011 | Saito | A61B 1/00009 600/109 |
| 2013/0182169 A1* | 7/2013 | Kosugi | G02B 23/2415 348/335 |
| 2016/0022125 A1* | 1/2016 | Nicolau | A61B 5/062 600/424 |
| 2017/0032539 A1* | 2/2017 | Kuramoto | A61B 1/043 |

FOREIGN PATENT DOCUMENTS

JP           5073564 B2      11/2012
WO      2012132638 A1        10/2012

* cited by examiner

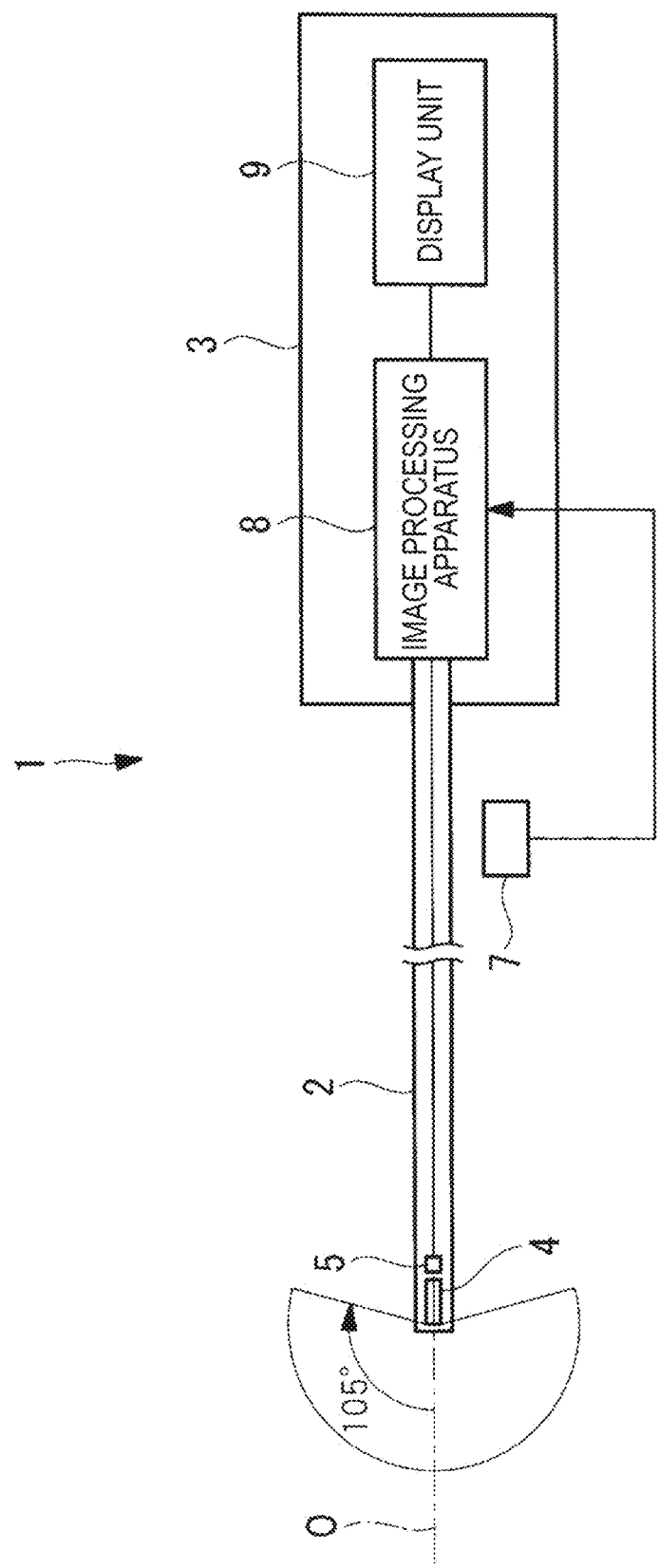

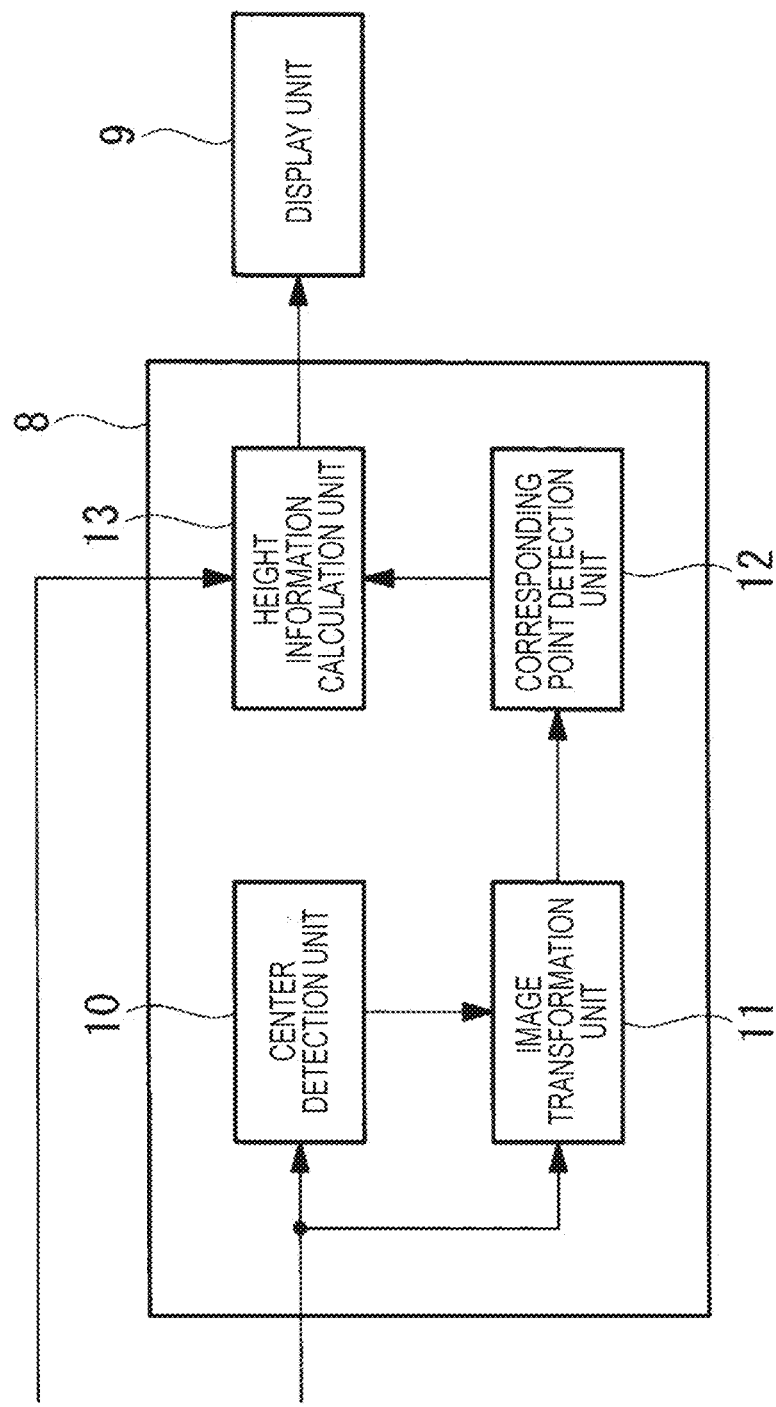

| AREA | CENTRAL COORDINATE x | CENTRAL COORDINATE y |
|------|----------------------|----------------------|
| A1   | xc1(246)             | yc1(281)             |
| A2   | xc2(246)             | yc2(280)             |
| A3   | xc3(246)             | yc3(276)             |
| A4   | xc4(246)             | yc4(276)             |

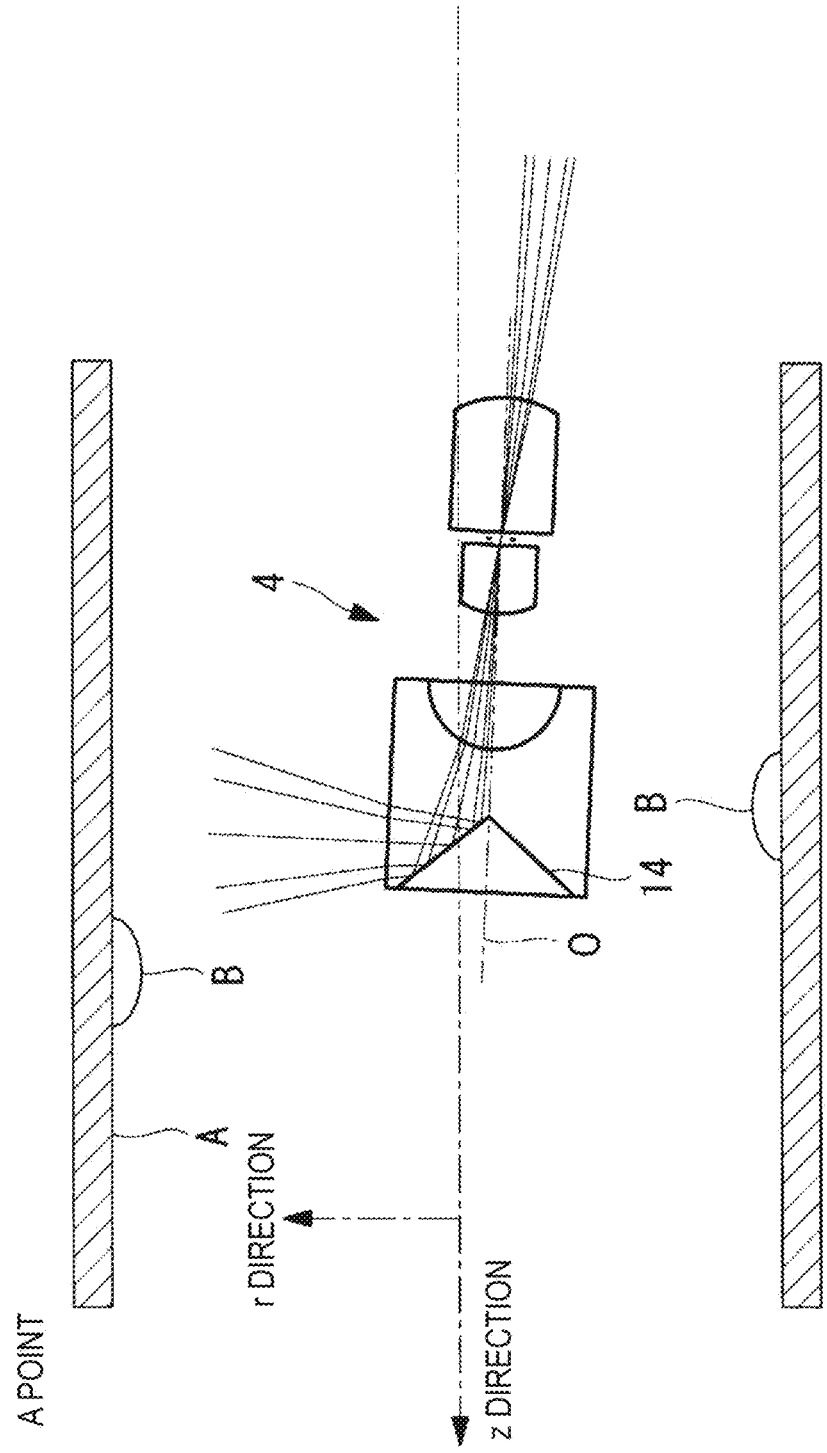

IMAGE PROCESSING APPARATUS, IMAGE PROCESSING METHOD, AND ENDOSCOPE

TECHNICAL FIELD

The present invention relates to an image processing apparatus, an image processing method, and an endoscope.

BACKGROUND ART

A method of acquiring disparity images in a stereo optical system and acquiring height information regarding a subject from the acquired disparity images, in observation with an endoscope, has been known.

SUMMARY OF INVENTION

Technical Problem

Some endoscopes simultaneously acquire two disparate images with two lenses disposed on the tip surface of an insertion unit. However, it is difficult to orient the tip surface of the insertion unit toward a subject when the subject is disposed on the internal surface of an elongated tubular organ, such as a digestive tract.

The present invention has been made in consideration of the issue, and an object of the present invention is to provide an image processing apparatus, an image processing method, and an endoscope, capable of acquiring height information regarding a subject disposed on the internal surface of an elongated tubular member.

Solution to Problem

According to one aspect of the present invention, In order to easily acquire height information regarding a subject disposed on the internal surface of an elongated tubular member, an image processing apparatus according to the present disclosure, includes a processor the processor including hardware and configured to perform the steps of receiving a first image and a second image acquired from a subject using an optical system having a field of view in a direction of at least about 90° to a central axis of the optical system, the first image acquired at a first position, the second image acquired at a second position, the second position different from the first position along the central axis; setting a first barycentric position of a first brightness value in the first image; setting a second barycentric position of a second brightness value in the second image; creating a third image by performing polar coordinate transformation to the first image with the first barycentric position; creating a fourth image by performing polar coordinate transformation to the second image with the second barycentric position; detecting corresponding points of the subject in the third image and in the fourth image; and calculating a distance between the subject and the central axis of the optical system, based on a distance between the first position and the second position, and based on the corresponding points in the third image and in the fourth image.

According to the present aspect, the image transformation unit receives the two images of the internal circumferential surface of the member to be observed, acquired by inserting the optical system inside the tubular member to be observed and performing the shooting at the two different locations in the longitudinal direction, and the distance between the shot positions of the two images. Then, the image transformation unit sets the central axis of the optical system to each of the images that have been received, to perform the polar coordinate transformation with the central axis. Then, the corresponding point detection unit detects the corresponding points of the two after-transformation images, and the distance calculation unit calculates the distance of the internal circumferential surface of the member to be observed from the central axis of the optical system, on the basis of the corresponding points that have been detected and the distance between the shot positions that has been input.

The distance of the internal circumferential surface from the central axis of the optical system is calculated with the images in the circumferential direction of the tubular member to be observed acquired by so-called side viewing of the optical system having the field of view in the direction of at least 90° to the central axis, so that height information regarding a subject disposed on the internal surface of the elongated tubular member to be observed, can be easily acquired.

According to the aspect, the image transformation unit may process each of the images that have been acquired, to set the central axis of the optical system.

When the two images are input into the image transformation unit with this arrangement, the image transformation unit processes each of the images and sets the central axis of the optical system, to perform the polar coordinate transformation with the central axis that has been set.

According to the aspect, the image transformation unit may segment each of the images that have been acquired, into a plurality of areas and set the central axis of the optical system to each of the areas that have been segmented, to perform the polar coordinate transformation.

When the central axis of the optical system inclines to the longitudinal direction of the tubular member to be observed, the central axis of the optical system varies between regions in each of the images. Thus, with the arrangement, the central axis is set to each of the areas that have been segmented, so that the central axis of the optical system set to the entirety of each of the images, can be artificially identical to the longitudinal direction of the tubular member. With this arrangement, the corresponding point detection can be precisely performed between the two images and the distance from the central axis can be precisely calculated.

According to a different aspect of the present invention, an image processing method includes: receiving a first image and a second image acquired by taking a subject using an optical system having a field of view in a direction of at least 90° to an central axis of the optical system, the first image being taken at a first position, the second image being taken at a second position different from the first position along the central axis; setting a first barycentric position of a first brightness values in the first image; setting a second barycentric position of a second brightness values in the second image; creating a third image by performing polar coordinate transformation to the first image with the first barycentric position; and creating a fourth image by performing polar coordinate transformation to the second image with the second barycentric position, detecting corresponding points of the subject in the third image and in the fourth image; and calculating a distance between the subject and the central axis of the optical system, based on a distance between the first position and the second position, and on the corresponding points in the third image and in the fourth image.

According to the aspect, the image transformation step may include a central axis setting step of processing each of the images that have been acquired, to set the central axis of the optical system.

According to the aspect, the central axis setting step may include segmenting each of the images that have been acquired, into a plurality of areas to set the central axis of the optical system to each of the areas that have been segmented.

According to a different aspect of the present invention, an endoscope includes: an image pickup unit including an optical system having a field of view in a direction of at least 90° to an central axis, the image pickup unit being to be input in a longitudinal direction inside a tubular member to be observed; a distance setting unit configured to set a traveled distance of the optical system of the image pickup unit in the longitudinal direction; and the image processing apparatus according to any of the aspects, the image processing apparatus being configured to process two images acquired by shooting an internal circumferential surface of the member to be observed, by the image pickup unit with the optical system traveling to different positions in the longitudinal direction.

According to the aspect, the optical system of the image pickup unit may have the field of view of more than 90° on one side to the central axis.

According to the aspect, the endoscope may further include a sensor configured to detect a travel amount of the optical system.

Advantageous Effects of Invention

According to the present invention, an effect in which height information regarding a subject disposed on the internal surface of an elongated tubular member can be acquired, is achieved.

BRIEF DESCRIPTION OF DRAWINGS

FIG. 1 is a block diagram of an endoscope according to an embodiment of the present invention.

FIG. 2 is a block diagram of an image processing apparatus according to the embodiment of the present invention, included in the endoscope of FIG. 1.

FIG. 10A is a longitudinal sectional view of the relationship between an observing optical system including a conic mirror and a tubular member to be observed, according to a modification of the endoscope of FIG. 1.

DESCRIPTION OF EMBODIMENTS

An endoscope 1 and an image processing apparatus 8 according to an embodiment of the present invention, will be described below with reference to the drawings.

The endoscope 1 according to the present embodiment, includes, as illustrated in FIG. 1, an elongated insertion unit (image pickup unit) 2 to be inserted into a tubular member or organ to be observed A, such as a digestive tract, and an apparatus body 3 connected to the base end of the insertion unit 2.

Figure 3A:
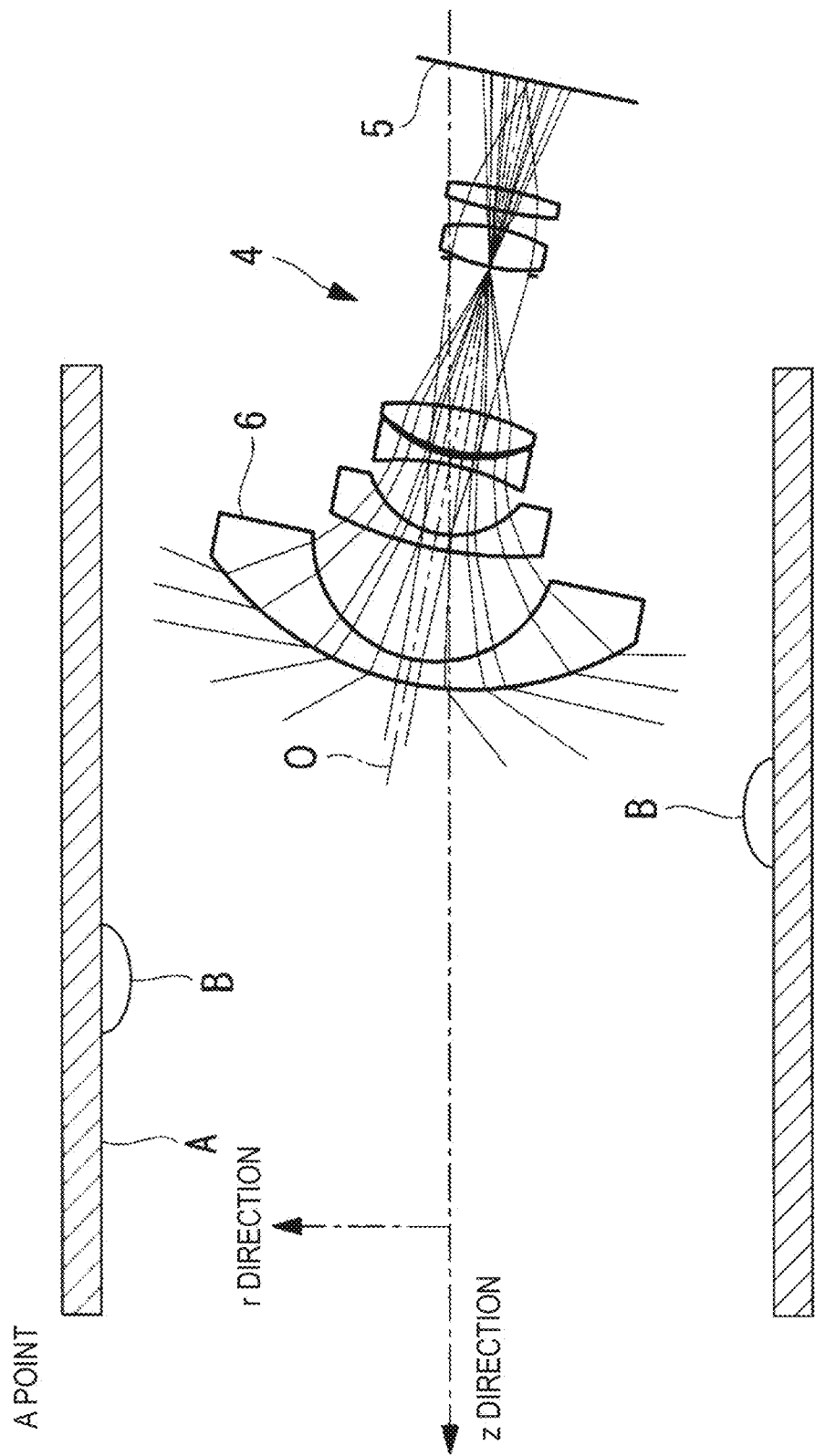
FIG. 3A is a longitudinal sectional view of the relationship between an observing optical system provided at the tip of an insertion unit of the endoscope of FIG. 1 and a tubular member to be observed.

The tip of the insertion unit 2 includes an observing optical system (optical system) 4 having a central axis O that is the same or substantially the same as the central axis in a longitudinal direction of the insertion unit 2, and an image pickup element 5, such as a CMOS sensor or other suitable sensor, that receives light condensed by the observing optical system 4, is disposed. For example, the observing optical system 4 includes, as illustrated in FIG. 3A, a fisheye lens 6 having an angle of view of more than about 90° on one side, for example, an angle of view of about 105° over the entire circumference.

As illustrated in FIG. 1, an insertion detection unit (distance setting unit) 7 that detects the travel amount (distance) in the longitudinal axial direction of the insertion unit 2, is provided on the side of the base end of the insertion unit 2. The insertion detection unit 7 includes, for example, a camera that images a scale displayed on the external surface of the insertion unit 2, and performs image processing to an image of the acquired scale to detect the position in the insertion direction of the insertion unit 2. In other embodiments, the distance setting unit 7 may be an input apparatus into which an operator reads the scale and then inputs the scale.

The apparatus body 3 includes the image processing apparatus 8 according to the present embodiment that processes signals from the image pickup element 5 and the insertion detection unit 7, and a display 9 that displays an image processed by the image processing apparatus 8. The image processing apparatus 8 is consisted of one or plural processors.

As illustrated in FIG. 2, the image processing apparatus 8 according to the present embodiment, includes: a center detection unit 10 that performs image processing to an image acquired by the image pickup element 5 to detect the position of the central axis O of the observing optical system 4 in the image; an image transformation unit 11 that performs polar coordinate transformation to the image, on the basis of the central axis O of the observing optical system 4 detected by the center detection unit 10; a corresponding point detection unit 12 that detects corresponding points of two images subjected to the polar coordinate transformation by the image transformation unit 11; and a height information calculation unit (distance calculation unit) 13 that calculates the distance of each corresponding point from the central axis, on the basis of the corresponding points detected by the corresponding point detection unit 12 and the positional distance in the longitudinal direction of the insertion unit 2 in time between the capturing of the two images, detected by the insertion detection unit 7. All of the center detection unit 10, the image transformation unit 11, the corresponding point detection unit 12 and the height information calculation unit 13 can be implemented in one processor. Each of the center detection unit 10, the image transformation unit 11, the corresponding point detection unit 12 and the height information calculation unit 13 can be implemented in one of different processors.

Figure 4A:
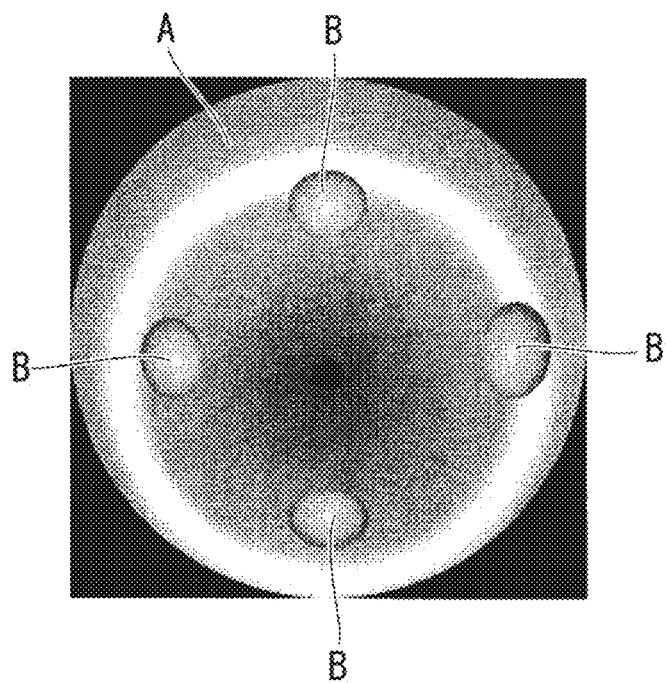
FIG. 4A is a graphic view of exemplary image of the member to be observed acquired by the endoscope of FIG. 3A.
Figure 4B:
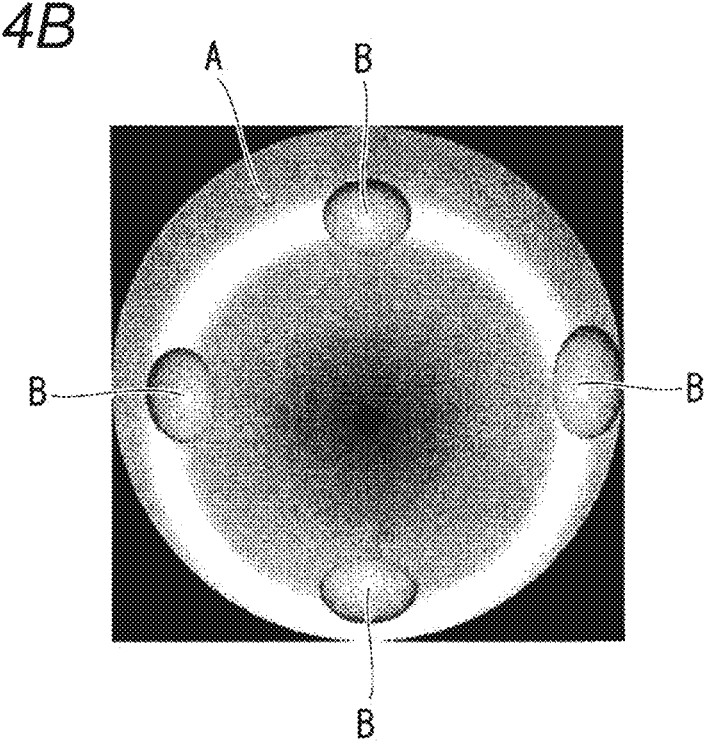
FIG. 4B is a graphic view of exemplary image of the member to be observed acquired by the endoscope of FIG. 3B.
Figures 5, 6:
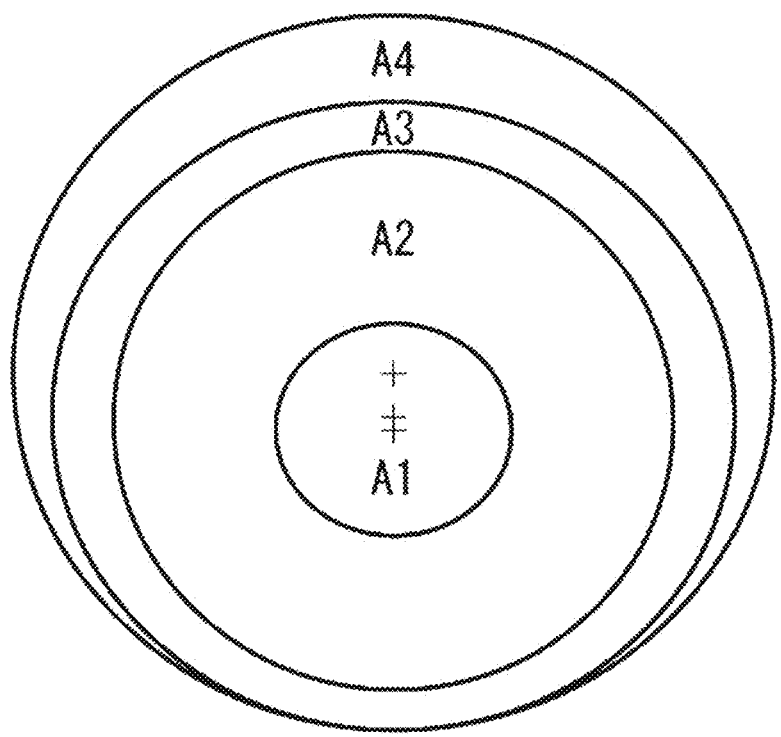
FIG. 5 is a diagram of barycentric positions detected in a plurality of areas including the image of FIG. 4B acquired in FIG. 3B, segmented, the barycentric positions being indicated in the respective areas.
FIG. 6 is a table of data including the barycentric positions detected in FIG. 5, the barycentric positions being organized for the respective areas.

The center detection unit 10 segments, on the basis of the distribution of brightness values in the entire image as illustrated in FIG. 4B acquired by the image pickup element 5, the image illustrated in FIG. 4B into a plurality of areas A1 to A4 as illustrated in FIG. 5, and calculates the barycentric positions of the brightness values for the respective segmented areas as indicated with a symbol of "+", to store the barycentric positions as a data point, as illustrated in FIG. 6.

The barycentric positions calculated by the center detection unit 10 indicate the central axis O of the observing optical system 4 arranged for the respective areas.

Therefore, the calculated barycentric positions are arranged on a substantially straight line, as illustrated in FIG. 5B. Thus, the center detection unit 10 excludes, as an error, a barycentric position a threshold value or more apart from the straight line. The threshold value can be set as half width of Gaussian function fitted in the barycentric positions calculated in the plurality of areas.

The image transformation unit 11 performs the polar coordinate transformation with the barycentric position $(xci, yci)$ for each area calculated by the center detection unit 10, in accordance with the following expressions:

$$R=\sqrt{(x-xci)^2+(y-yci)^2}$$

$$\theta=\tan^{-1}((x-xci)/(y-yci))$$

where R represents the distance in a radial direction from the central axis O of the observing optical system 4 and $\theta$ represents the angle around the central axis O of the observing optical system 4.

Figure 7A:
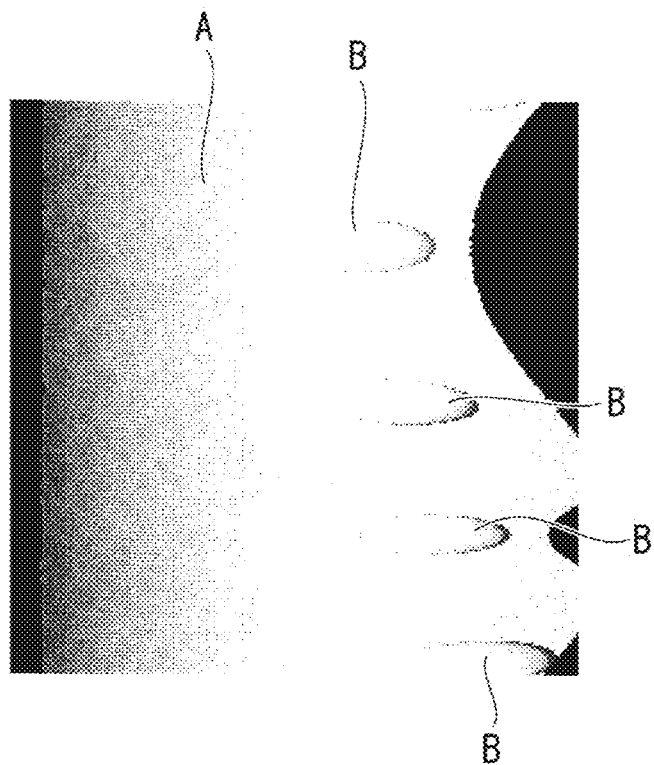
FIG. 7A is a graphic view of an exemplary image including the image of FIG. 4A subjected to polar coordinate transformation.
Figure 7B:
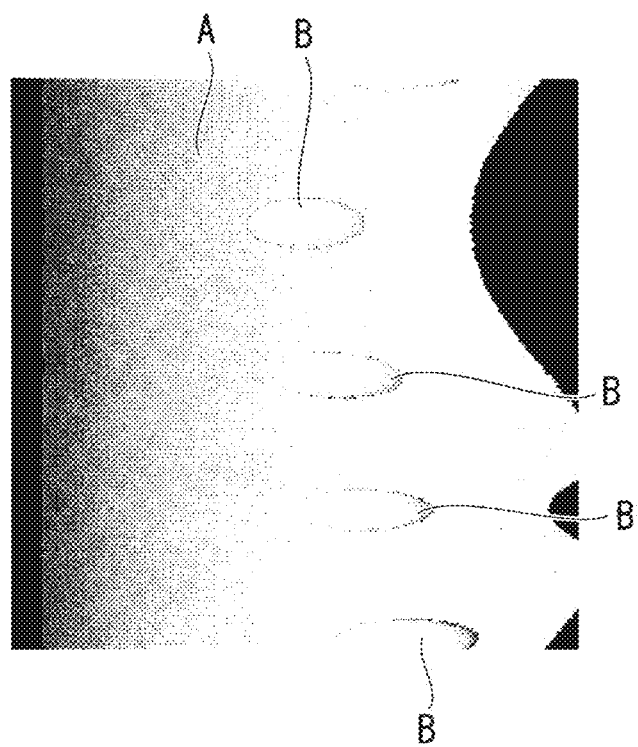
FIG. 7B is a graphic view of an exemplary image including the image of FIG. 4B subjected to polar coordinate transformation.

This arrangement generates images subjected to the polar coordinate transformation, as illustrated in FIGS. 7A and 7B.

Figure 3B:
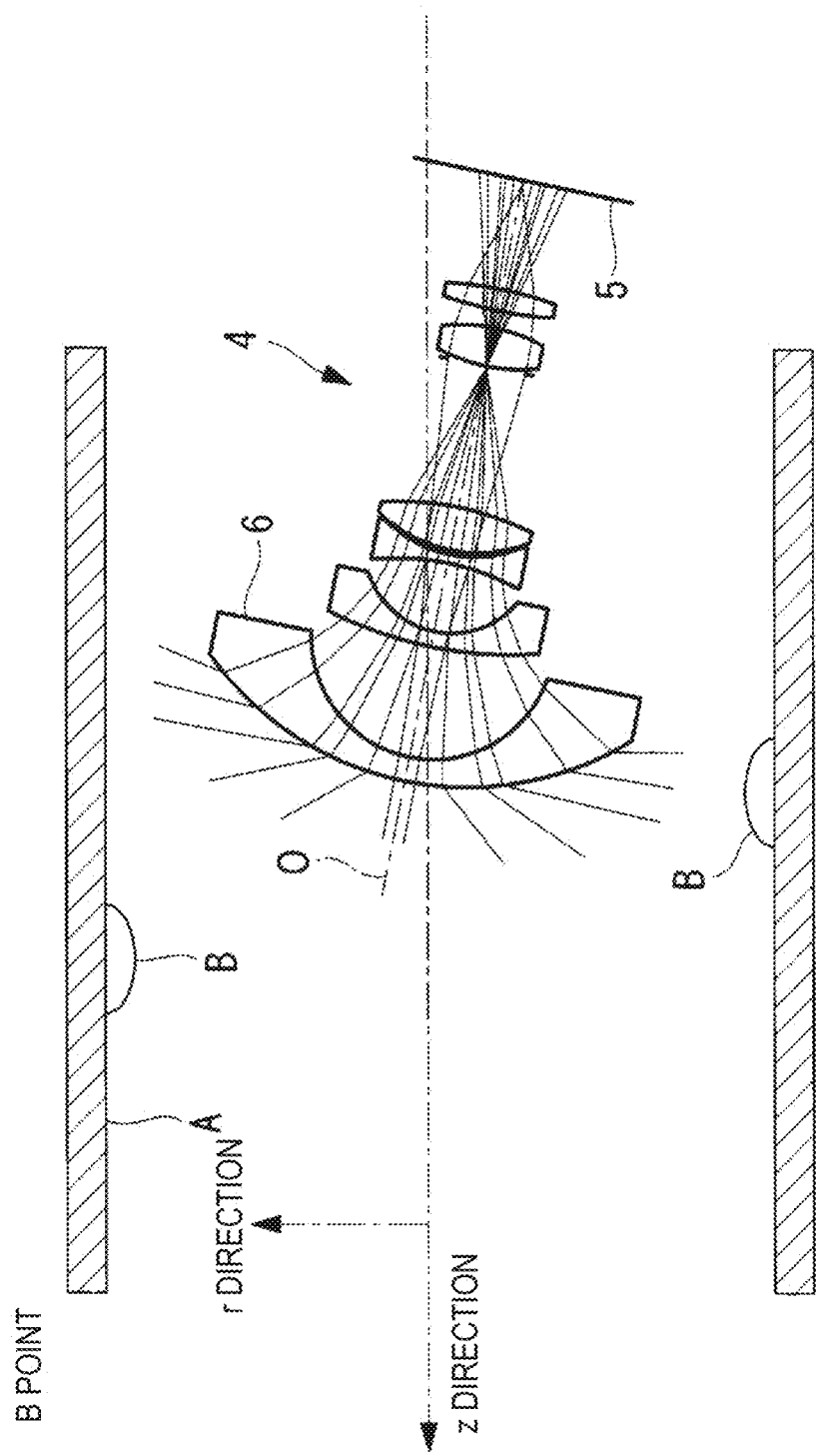
FIG. 3B is a longitudinal sectional view of the insertion unit of FIG. 3A moved forward in the longitudinal axial direction of the member to be observed.

The detection of the barycentric positions by the center detection unit 10 and the polar coordinate transformation by the image transformation unit 11 are performed to two images, as illustrated in FIGS. 4A and 4B, acquired by the image pickup element 5 at two locations between which the position in the longitudinal direction of the insertion unit 2 varies, as illustrated in FIGS. 3A and 3B.

Then, the image transformation unit 11 transmits the two after-transformation images that have been subjected to the polar coordinate transformation, to the corresponding point detection unit 12, and then the corresponding point detection unit 12 detects corresponding points between the two images, with template matching processing, such as an SSD method (Sum of Squared Difference method).

The difference in the number of pixels between the corresponding points detected by the corresponding point detection unit 12 and the travel amount of the insertion unit 2 between the image capture positions of the two images detected by the insertion detection unit 7, are input into the height information calculation unit 13, so that the distance from the central axis O of the observing optical system 4 detected by the center detection unit 10, is calculated with a triangulation method, on the basis of the difference in the number of pixels between the corresponding points and the travel amount of the insertion unit 2. In general, the triangulation method requires a base line and two angles from two points on the base line to a measuring point. In this case, the base line is the central axis O, the two points are both end of the travel amount of the insertion unit 2, the measuring point is the corresponding point in two images, and the two angle can be calculated from the number of pixels between the corresponding points. Accordingly the distance from the central axis O to the corresponding point can be calculated with a triangulation method.

Figure 8:
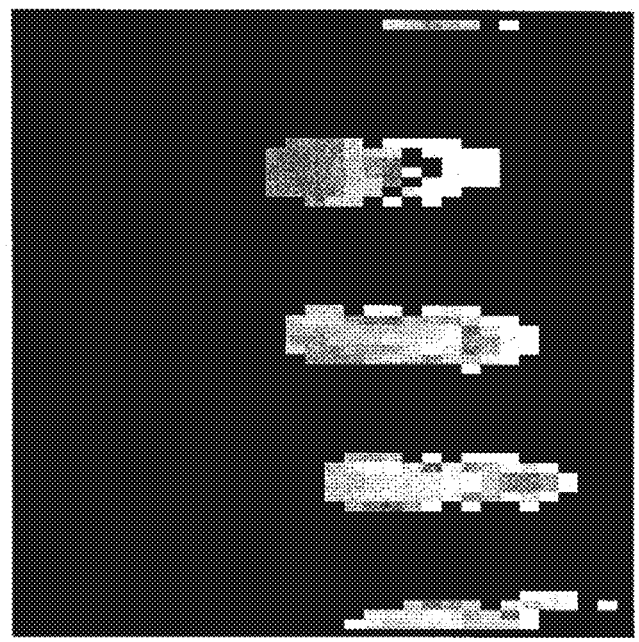
FIG. 8 is a graphic view of height information calculated from the images of FIGS. 7A and 7B.

Then, for example, as illustrated in FIG. 8, an image including the distance (height information) from the central axis O calculated by the height information calculation unit 13, displayed on the corresponding point position of the last acquired image, is generated and then output to the display 9. For the image display of the height information, for example, color may vary in accordance with the distance in magnitude.

An image processing method with the image processing apparatus 8 according to the present embodiment with this configuration, will be described below.

In order to detect height information regarding each region present in an image, with the image processing apparatus 8 according to the present embodiment, the insertion unit 2 is inserted into the tubular member or organ to be observed A, and then two images are acquired with the position in the longitudinal direction of the insertion unit 2 varying in proximity to a position at which the height information is to be detected.

Figure 9:
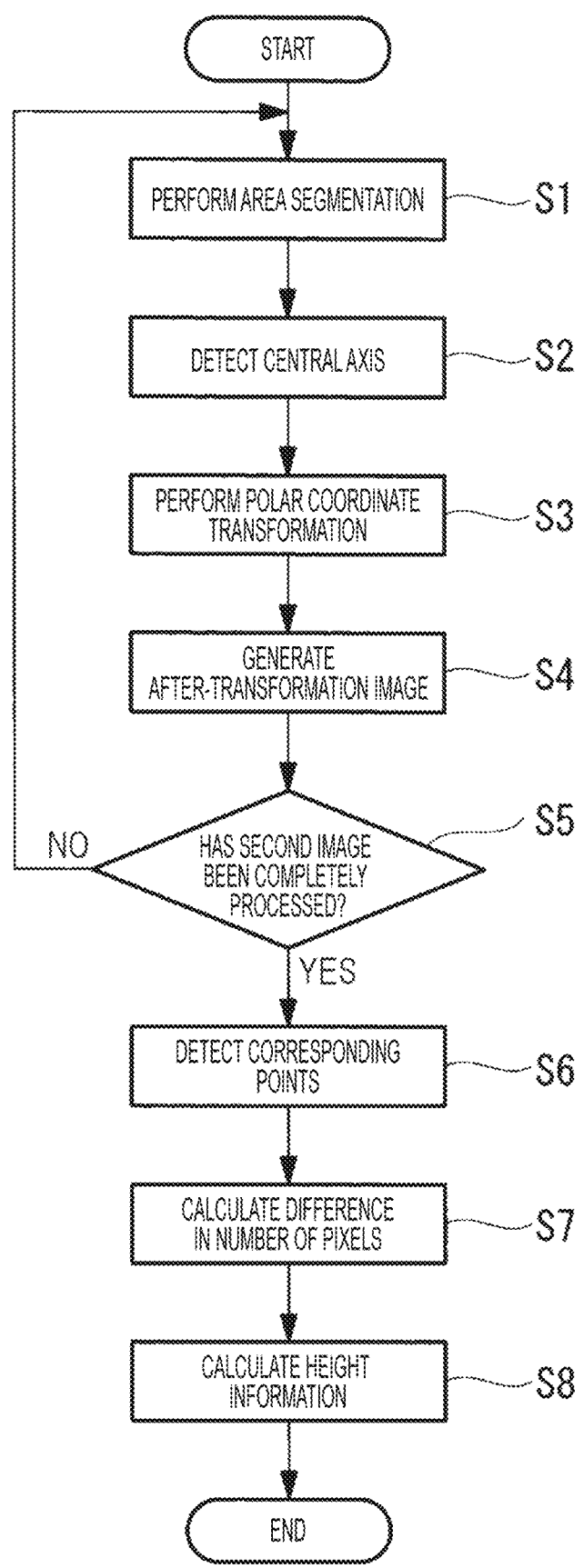
FIG. 9 is a flowchart for describing an image processing method with the image processing apparatus of FIG. 2.

Referring to FIG. 9, when the acquired two images and the travel amount of the insertion unit 2 are input into the image processing apparatus 8, the area segmentation is performed to the first image on the basis of the distribution of brightness values (step S1). Then, the center detection unit 10 detects the central axis O of the observing optical system 4 for each segmented area (central axis setting step S2). After that, the polar coordinate transformation is performed to each area with the detected central axis O (step S3). Then, the respective images of the areas after the transformation are combined with each other, and an after-transformation image is generated (image transformation step S4). Next, it is determined whether the second image has been completely processed (step S5) and then, if the second image has not been completely processed, the process is repeated for the second image from step S1.

Then, after the generation of the after-transformation images for the two images, corresponding points are detected between the generated after-transformation images (corresponding point detection step S6), and the difference in the number of pixels between the detected corresponding points is calculated (step S7). The distance of each of the detected corresponding points from the central axis O of the observing optical system 4 is calculated with a suitable triangulation method on the basis of the calculated difference in the number of pixels and the travel amount input from the insertion detection unit 7 (distance calculation step S8).

The endoscope 1 according to the present embodiment, has an advantage in that the height information regarding each region B on the internal surface of the member to be observed A, can be acquired with the insertion unit 2 disposed in the longitudinal axial direction of the member to be observed A without a need to orient the tip surface of the insertion unit 2 toward the internal surface of the tubular member to be observed A.

The image processing apparatus 8 and the image processing method according to the present embodiment, have an advantage in that the height information regarding each region B on the internal surface of the tubular member to be observed A, can be acquired on the basis of the images acquired by the observing optical system 4 having the angle of view more than 90° on the one side from the central axis.

With the endoscope 1 and the image processing apparatus 8, are of an arrangement having an advantage in that even when the central axis O of the observing optical system 4 inclines to the longitudinal axis of the tubular member to be observed A as illustrated in FIGS. 3A and 3B, the precision of the polar coordinate transformation can improve with the angle of inclination artificially set to zero.

Note that, according to the present embodiment, the segmentation is made to acquire the plurality of annular areas each surrounding the central axis, on the basis of the brightness values, but a different method may be used for the segmentation, instead of this.

According to the present embodiment, the observing optical system 4 has the angle of view of about 105° on the one side from the central axis O, but may have an angle of view of more than about 90° instead.

Figure 10B:
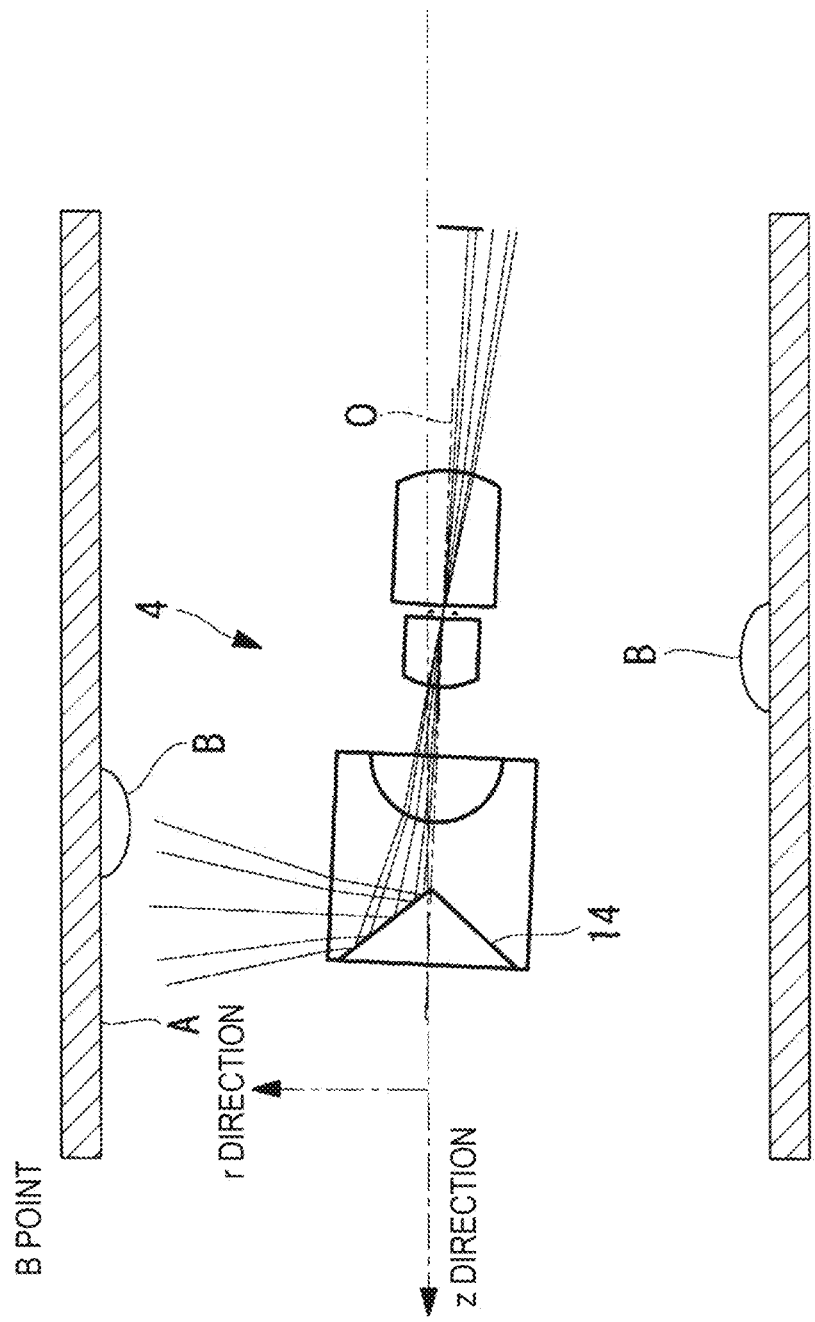
FIG. 10B is a longitudinal sectional view of an insertion unit of FIG. 10A moved forward in a longitudinal axial direction of the member to be observed.
Figure 11A:
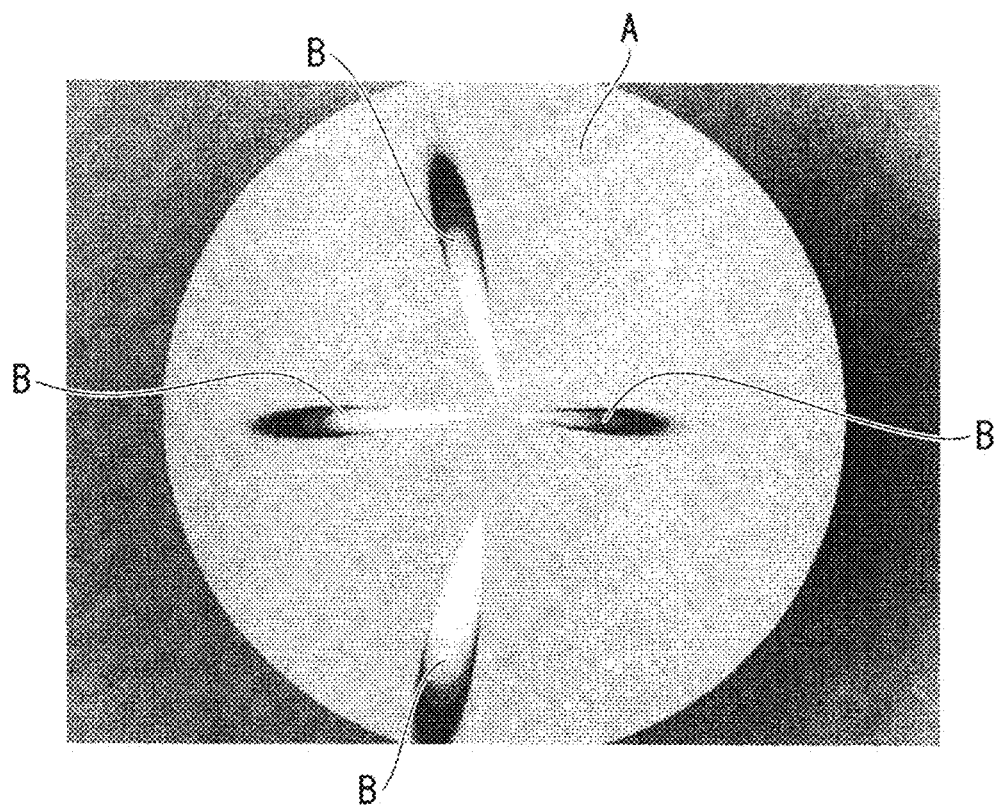
FIG. 11A is a graphic view of an image of the member to be observed acquired by the endoscope of FIG. 10A.
Figure 11B:
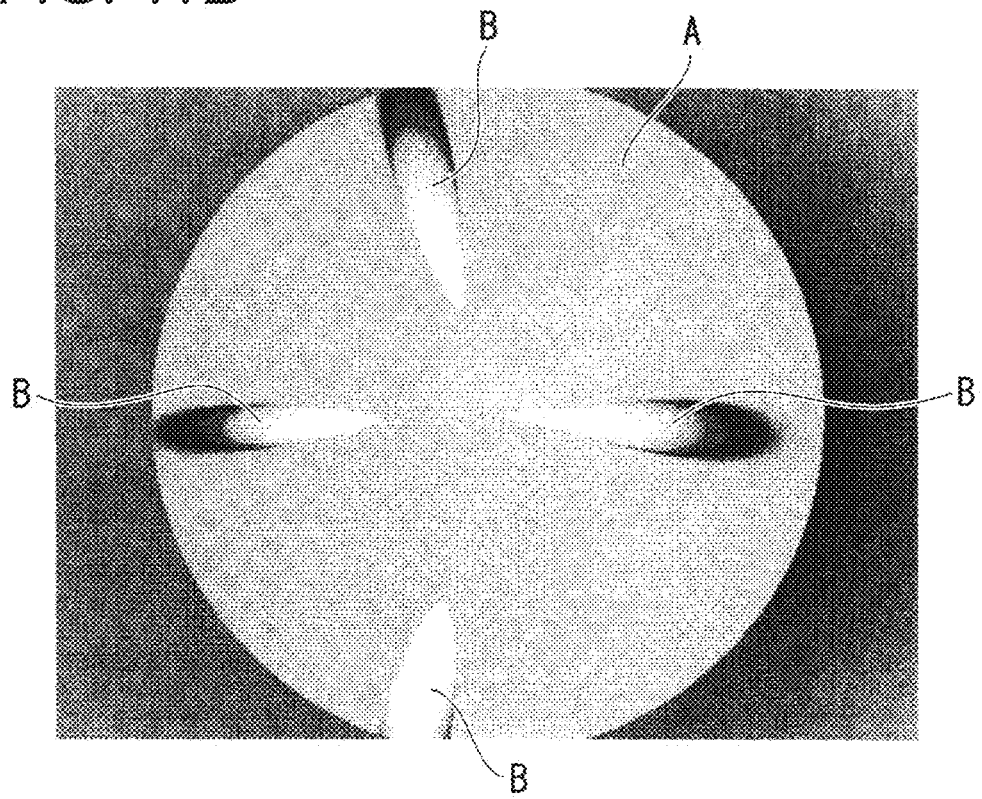
FIG. 11B is a graphic view of an image of the member to be observed acquired by the endoscope of FIG. 10B.

According to the present embodiment, the case where the observing optical system 4 includes the fisheye lens 6 having the angle of view of about 105° on the one side from the central axis O, has been described, but an observing optical system 4 including a conic mirror 14 as illustrated in FIGS. 10A and 10B may be adopted instead. This arrangement allows the entire circumference of the internal surface of the member to be observed A disposed in a range of about 70° to about 110° to the central axis O, to be observed, so that images as illustrated in FIGS. 11A and 11B can be acquired.

Figure 12A:
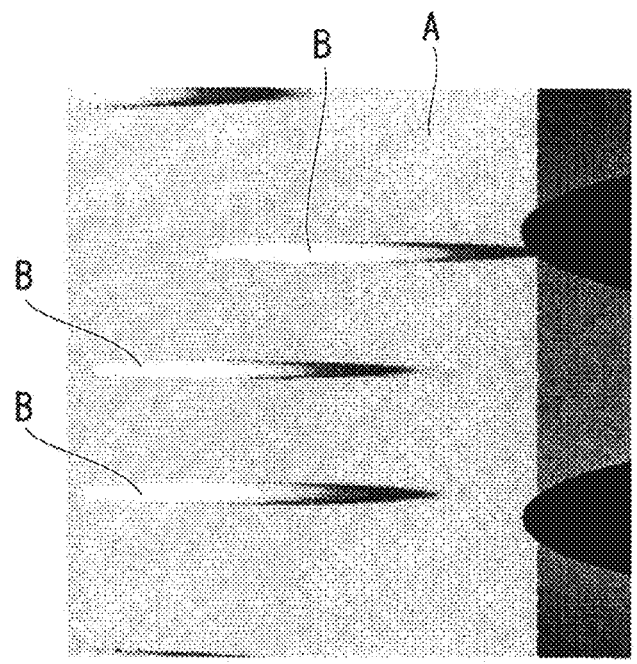
FIG. 12A is a graphic view of an image including the image of FIG. 11A subjected to polar coordinate transformation.
Figure 12B:
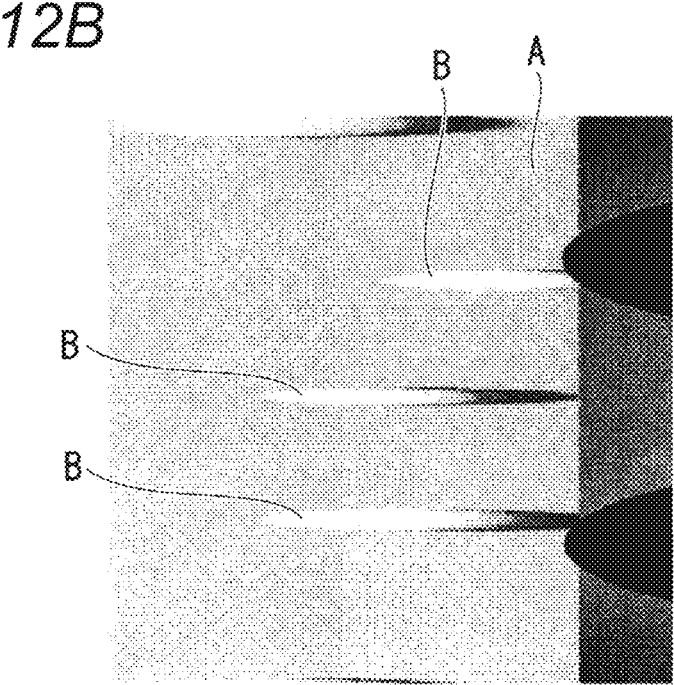
FIG. 12B is a graphic view of an image including the image of FIG. 11B subjected to the polar coordinate transformation.
Figure 13:
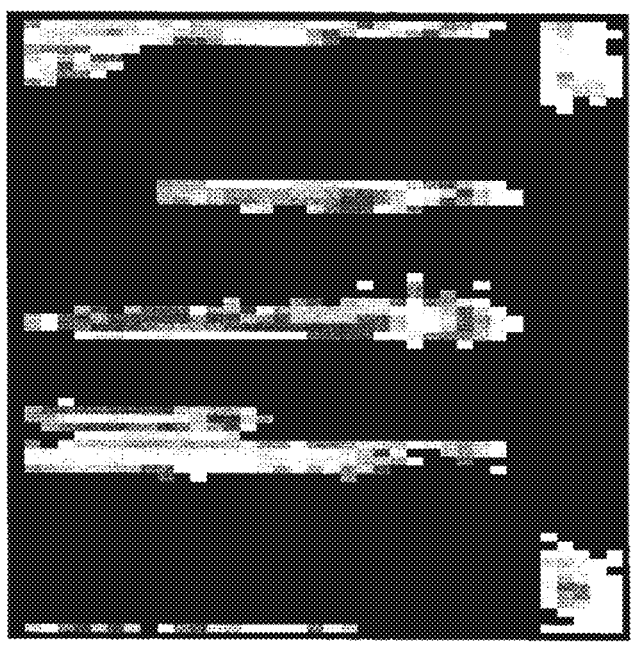
FIG. 13 is a graphic view of height information calculated from the images of FIGS. 12A and 12B.

In this case, the detection of the central axis O of the observing optical system 4 and the polar coordinate transformation are performed to each of the acquired two images. Then, corresponding points are detected for after-transformation images as illustrated in FIGS. 12A and 12B and height information is calculated for the detected corresponding points, so that the height information regarding each region B on the internal surface of the tubular member to be observed A can be acquired as illustrated in FIG. 13.

Instead, an observing optical system including an objective lens that internally reflects lateral light twice to orient the lateral light toward an image pickup element, may be adopted.

The images acquired by the camera are processed in order to detect the travel amount of the insertion unit 2. However, instead of this, a position sensor, such as a GPS sensor, may detect the travel amount.

REFERENCE SINGS LIST

1 Endoscope
2 Insertion unit (image pickup unit)
4 Observing optical system (optical system)
7 Insertion detection unit (distance setting unit)
8 Image processing apparatus
11 Image transformation unit
12 Corresponding point detection unit
13 Height information calculation unit (distance calculation unit)
S2 Central axis setting step
S4 Image transformation step
S6 Corresponding point detection step
S8 Distance calculation step
A Member to be observed
O Central axis

The invention claimed is:

1. An image processing apparatus comprising a processor, the processor comprising hardware and configured to perform the steps of:
   receiving a first image and a second image acquired from a subject using an optical system having a field of view in a direction of at least about 90° to a central axis of the optical system, the first image acquired at a first position, the second image acquired at a second position, the second position different from the first position along the central axis;
   setting a first barycentric position of a first brightness value in the first image;
   setting a second barycentric position of a second brightness value in the second image;
   creating a third image by performing polar coordinate transformation to the first image with the first barycentric position;
   creating a fourth image by performing polar coordinate transformation to the second image with the second barycentric position;
   detecting corresponding points of the subject in the third image and in the fourth image; and
   calculating a distance between the subject and the central axis of the optical system, based on a distance between the first position and the second position, and based on the corresponding points in the third image and in the fourth image.

2. The image processing apparatus according to claim 1, wherein the processor is further configured to perform the steps of:
   after receiving a first image and a second image, before setting the first barycentric position, segmenting each of the first image and the second image into a plurality of areas on the basis of the first brightness value and the second brightness value,
   wherein the first barycentric position and the second barycentric position are set in each of the plurality of areas of each of the first image and the second image.

3. The image processing apparatus according to claim 1, wherein the processor is further configured to calculate a distance between the subject and the central axis of the optical system, with a triangulation method using the distance between the first position and the second position, and a distance between corresponding points in the third image and the fourth image.

4. An image processing method comprising the steps of:
   receiving a first image and a second image acquired by taking a subject using an optical system having a field of view in a direction of at least 90° to an central axis of the optical system, the first image being taken at a first position, the second image being taken at a second position different from the first position along the central axis;

setting a first barycentric position of a first brightness values in the first image;

setting a second barycentric position of a second brightness values in the second image;

creating a third image by performing polar coordinate transformation to the first image with the first barycentric position; and creating a fourth image by performing polar coordinate transformation to the second image with the second barycentric position, detecting corresponding points of the subject in the third image and in the fourth image; and calculating a distance between the subject and the central axis of the optical system, based on a distance between the first position and the second position, and on the corresponding points in the third image and in the fourth image.

5. The image processing method according to claim 4, further comprising the steps of:

after receiving a first image and a second image, before setting the first barycentric position, segmenting each of the first image and the second image into a plurality of areas on the basis of the first brightness value and the second brightness value, wherein the first barycentric position and the second barycentric position are set in each of the plurality of areas of each of the first image and the second image.

6. The image processing method according to claim 5, wherein the processor is further configured to calculate a distance between the subject and the central axis of the optical system, with a triangulation method using the distance between the first position and the second position, and a distance between corresponding points in the third image and the fourth image.

7. An endoscope comprising:

an image sensor configured to form the first image and the second image;

a distance detector configured to set the distance between the first position and the second position; and the image processing apparatus according to claim 1.

8. The endoscope according to claim 7, wherein the optical system has the field of view of more than about 90° on one side to the central axis.

9. The endoscope according to claim 7, further comprising: a sensor configured to detect a distance between the first position and the second position.

* * * * *